US010131714B2

(12) United States Patent
Duthe et al.

(10) Patent No.: US 10,131,714 B2
(45) Date of Patent: Nov. 20, 2018

(54) PROTEIN PURIFICATION USING BIS-TRIS BUFFER

(75) Inventors: Didier Duthe, Paris (FR); Laure Landric-Burtin, Paris (FR); Benoit Mothes, Paris (FR)

(73) Assignee: SANOFI, Paris (FR)

( * ) Notice: Subject to any disclaimer, the term of this patent is extended or adjusted under 35 U.S.C. 154(b) by 241 days.

(21) Appl. No.: 14/360,103

(22) PCT Filed: May 23, 2012

(86) PCT No.: PCT/EP2012/059528
§ 371 (c)(1),
(2), (4) Date: May 22, 2014

(87) PCT Pub. No.: WO2013/075849
PCT Pub. Date: May 30, 2013

(65) Prior Publication Data
US 2014/0323698 A1    Oct. 30, 2014

(30) Foreign Application Priority Data

Nov. 23, 2011  (WO) ................. PCT/EP2011/070768

(51) Int. Cl.
| | | |
|---|---|---|
| C07K 16/40 | (2006.01) |
| C07K 1/16 | (2006.01) |
| C07K 1/36 | (2006.01) |
| B01D 15/38 | (2006.01) |
| C07K 16/12 | (2006.01) |
| C07K 16/18 | (2006.01) |

(52) U.S. Cl.
CPC .......... *C07K 16/40* (2013.01); *B01D 15/3809* (2013.01); *C07K 1/165* (2013.01); *C07K 1/36* (2013.01); *C07K 16/12* (2013.01); *C07K 16/18* (2013.01)

(58) Field of Classification Search
CPC .......... C07K 16/40; C07K 1/165; C07K 1/36; C07K 16/12; C07K 16/18; B01D 15/3809
See application file for complete search history.

(56) References Cited

U.S. PATENT DOCUMENTS

| | | | | |
|---|---|---|---|---|
| 5,891,741 A | * | 4/1999 | Siiman ................. G01N 33/533 | |
| | | | | 436/529 |
| 6,602,855 B2 | * | 8/2003 | Jackowski ......... G01N 33/6893 | |
| | | | | 436/173 |
| 2002/0009445 A1 | | 1/2002 | Du et al. | |
| 2007/0259453 A1 | * | 11/2007 | Engstrand ............ B01D 15/327 | |
| | | | | 436/547 |
| 2009/0304710 A1 | * | 12/2009 | Park ................... C07K 16/2896 | |
| | | | | 424/158.1 |
| 2011/0065901 A1 | | 3/2011 | Soice et al. | |
| 2011/0073548 A1 | | 3/2011 | Williams et al. | |
| 2011/0237781 A1 | | 9/2011 | Lebing et al. | |
| 2012/0065380 A1 | | 3/2012 | Yoo et al. | |
| 2012/0238730 A1 | | 9/2012 | Dong et al. | |
| 2012/0322099 A1 | * | 12/2012 | Lapen ....................... G01N 1/30 | |
| | | | | 435/40.5 |
| 2013/0295082 A1 | | 11/2013 | Garidel et al. | |
| 2014/0018525 A1 | * | 1/2014 | Goklen .................... C07K 1/22 | |
| | | | | 530/416 |
| 2014/0323698 A1 | | 10/2014 | Duthe et al. | |

FOREIGN PATENT DOCUMENTS

| | | | |
|---|---|---|---|
| CN | 1266907 A | 9/2000 | |
| CN | 1814775 A | 8/2006 | |
| CN | 101730707 B | 12/2014 | |
| EP | 2 360 183 A1 | 8/2011 | |
| EP | 2 415 779 A1 | 2/2012 | |
| JP | 2008-501317 A | 1/2008 | |
| JP | 2008-517906 A | 5/2008 | |
| JP | 2008-533977 A | 8/2008 | |
| TW | 201313735 A | 4/2013 | |
| WO | WO 8903840 A1 * | 5/1989 | .............. B01J 39/26 |
| WO | 1995/008574 A1 | 3/1995 | |
| WO | 2005/103084 A2 | 11/2005 | |
| WO | 2006/043895 A1 | 4/2006 | |
| WO | 2006/099875 A1 | 9/2006 | |
| WO | 2009/007451 A1 | 1/2009 | |
| WO | 2009/111347 A1 | 9/2009 | |
| WO | 2010/071208 A1 | 6/2010 | |
| WO | 2010/082894 A1 | 7/2010 | |
| WO | 2011/049798 A1 | 4/2011 | |
| WO | 2012/135415 A1 | 10/2012 | |
| WO | 2013/028330 A2 | 2/2013 | |
| WO | 2013/075740 A1 | 5/2013 | |

OTHER PUBLICATIONS

Zhou et al., Purification and Characterization of the Prohormone Convertase PCl(PC3), The Journal of Biological Chemistry, 268(8), 5615-5623, 1993.*
GE Healthcare, Rapid process development for purification of a MAb using ÄKTA™ avant 25, 2009, pp. 1-8, retrieved from https://www.gelifesciences.com/gehcls_images/GELS/Related% 20Content/Files/1314787424814/litdoc28957347AB_20110831143417. pdf on Jun. 9, 2016.*
Riodan et al., Design of Salt-Tolerant Membrane Adsorbers for Viral Clearance, Biotechnol. Bioeng. 2009;103: 920-929.*
Bruel et al., Rhodopsin Kinase: Two mAbs binding near the carboxyl terminus cause time-dependent inactivation, PNAS, 2000, 90(7), 3010-3015.*
GE Healthcare Life Science, Multimodal Chromatography Handbook, 116 pages, retrieved from http://proteins.gelifesciences. com/~/media/protein-purification-ib/documents/handbooks/multimodal_ chromatography.pdf?la=en on Jan. 4, 2017.*
Horio et al.: Eds. (2000) "12.2 Good's buffer," Basic Experimental Methods for Proteins and Enzymes (in Japanese). Revised 2nd Version. pp. 554-555. (a Japanese experimental protocol book in which Table 12-2 "Good's buffers" shows Bis-Tris at the second line, the relevant portion of this document).

(Continued)

*Primary Examiner* — Andrea S Grossman
(74) *Attorney, Agent, or Firm* — Lathrop Gage LLP; James H. Velema, Esq.

(57) ABSTRACT

The invention provides a two-step chromatography process for small and large-scale purification of proteins, specifically monoclonal antibodies, using only four buffer solutions made from a mother solution.

20 Claims, 6 Drawing Sheets

(56) References Cited

OTHER PUBLICATIONS

Liu et al. (2010) "Recovery and purification process development for monoclonal antibody production," mAbs 2 (5):480-499.

Qian et al. (2007) "Conjugating recombinant proteins to Pseudomonas aeruginosa ExoProtein A: A strategy for enhancing immunogenicity of malaria vaccine candidates," Vaccine. 25(20):3923-3933.

Verdoliva et al. (2002) "Affinity purification of polyclonal antibodies using a new all-D synthetic peptide ligand: comparison with protein A and protein G," J. Immunol. Methods. 271(1-2):77-88.

International Search Report with Written Opinion corresponding to International Patent Application No. PCT/EP2012/059528, dated Jul. 26, 2012.

Eriksson et al. (Feb. 2009) "MAb Contaminant Removal with a Multimodal Anion Exchanger," BioProcess International. 7(2):52-56.

Landric-Burtin et al. (2011) "How to shorten downstream processing for Monoclonal antibodies," Presentation by Sanofi-Aventis, Biologics Center. European Downstream Technology Forum, May 24-25, 2011, Goettingen, Germany. 24 pages.

Japan Biochemical Society: Eds. (1990) Protein I: Isolation, Purification and Properties. 1st Ed. pp. 324-327.—provided with an English machine translation.

Follman et al. (2004) "Factorial screening of antibody purification processes using three chromatography steps without protein A," J. Chromatogr. A. 1024:79-85.

Pollock et al. (Jan. 25, 2013) "Optimising the design and operation of semi-continuous affinity chromatography for clinical and commercial manufacture," J. Chromatogr. A. 1284:17-27.

Written Opinion corresponding to International Patent Application No. PCT/EP2014/059246, dated Jul. 17, 2014, 12 pp.

Uwe Gottschalk (2008) "Bioseparation in Antibody manufacturing: the good, the bad and the ugly" Biotechnol. Prog, 24, 496-503.

Cristiana Boi (2007) "Membrane absorbers as purificaiton tools for monoclonal antibody purificaiton" J. Chromatography B, 848, 19-27.

\* cited by examiner

PROTEIN PURIFICATION USING BIS-TRIS BUFFER

CROSS-REFERENCE TO RELATED APPLICATIONS

This application is a 371 National Phase Entry application of co-pending International Application No. PCT/EP2012/059528, filed May 23, 2012, which claims the benefit of priority of International Application No. PCT/EP2011/070768, filed Nov. 23, 2011 which is hereby incorporated by reference in its entirety.

TECHNICAL FIELD

The invention relates to a two-step chromatography process for small and large-scale purification of proteins, specifically monoclonal antibodies, using four buffer solutions.

BACKGROUND

Antibody purification can be one of the most costly aspects of bioproduction. Monoclonal antibodies (mAbs) are generally purified using a three-step, three resin chromatography process, using a specific buffer system at each step. This conventional purification process encompasses a capture step, followed by an ionic exchange step, and concludes with a polishing step, and usually takes 3 to 5 working days (including storages and open phases). With increasing cell culture titers and larger cell culture volumes being used for production, downstream processing is viewed as an industry bottleneck. This is particularly relevant to monoclonal antibody production, where the focus has shifted away from batch volume, and towards downstream processing capacity. Furthermore, early pre-clinical and clinical phase studies require larger amounts of antibodies that can be produced more rapidly. Therefore, a need exists in the industry both for a reduction in the number of steps to be used for antibody purification, and in the time taken for obtaining batches.

SUMMARY OF INVENTION

The inventors have found a new method for purifying antibodies, said method comprising a limited numbers of steps while still allowing obtaining high yields of purified antibodies with an excellent degree of purity. The purified proteins are thus suitable for medical applications. Accordingly, the method may be used to purify proteins for clinical trials and/or for marketing of a pharmaceutical composition comprising the protein.

Briefly, this method comprises only two chromatographic steps: one affinity chromatography, and one multi-modal resin chromatography. In addition, it has been found that all buffers used during these two chromatography steps can be prepared starting from the same mother solution. In other terms, all buffers can consist of the same chemicals, although the concentrations of said chemicals may vary from one buffer to another. These buffers advantageously comprise Bis Tris, for example in combination with NaCl, acetic acid and water. As there is no need for any buffer exchange, the method is easy to carry out, and is highly suitable for automation and/or for running in continuous mode. In addition, the fact that all buffers can consist of the same chemicals allows greatly reducing the time for preparing the chromatographic columns, and also diminishes the need for manual interventions. The method of the invention further allows reducing or abolishing open phases (i.e. steps where the purification system is opened to carry out a manual operation such as preparing the chromatographic column for a new buffer, diluting the sample, or adjusting its pH), thereby reducing the risk of contamination. Therefore, the method of the invention allows both rapid production of batches and reducing the occupation time of the purification systems. It is thus suitable for scale-up and purification of recombinant proteins at an industrial scale.

Two specific protocols have been set up and implemented for three different antibodies. In a first protocol, the pH of the crude protein eluent obtained at the end of the first chromatographic step is adjusted using a Bis Tris solution (see Examples 3, 4 and 5). It has been shown that this protocol is universal insofar it gives excellent and reproducible results irrespective of the specific antibody that is purified (see Example 6). In a second protocol, the crude protein eluent obtained at the end of the first chromatographic step is directly passed over the second chromatography column, i.e. without undergoing any treatment like pH adjustment, buffer exchange or dilution (see Example 7). In this protocol, the two chromatographic steps may be followed by a passage over a membrane adsorber. This second protocol has the advantage of being extremely rapid (about 7 or 8 hours for 100 L of starting material). In addition, it can be completely automated, run in continuous mode, and it does not comprise any open phase.

The invention thus provides a method for purifying a protein from solution comprising a first chromatography step comprising passing equilibration buffer over a first chromatography column, passing the solution over the first chromatography column, passing equilibration buffer over the first chromatography column, passing wash and sanitation buffer over the first chromatography column, passing equilibration buffer over the first chromatography column, eluting a crude protein eluent from the first chromatography column using a first elution buffer, and optionally adjusting the pH of the crude protein eluent using a Bis Tris solution; and a second chromatography step comprising passing equilibration buffer over a second chromatography column, passing the crude protein eluent over the second chromatography column, passing equilibration buffer over the second chromatography column, and recovering purified protein from the second chromatography column using a second elution buffer.

The invention also provides a method for purifying a protein from solution comprising a first chromatography step comprising passing equilibration buffer over a first chromatography column, passing the solution over the first chromatography column, passing equilibration buffer over the first chromatography column, eluting a crude protein eluent from the first chromatography column using a first elution buffer, and optionally adjusting the pH of the crude protein eluent using a Bis Tris solution; and a second chromatography step comprising passing equilibration buffer over a second chromatography column, passing the crude protein eluent over the second chromatography column, passing equilibration buffer over the second chromatography column, passing wash and sanitation buffer over the second chromatography column, passing equilibration buffer over the second chromatography column, and recovering purified protein from the second chromatography column using a second elution buffer.

In one embodiment of the invention, the Bis Tris solution is a 1M Bis Tris solution. In other embodiments, each of the buffers comprises Bis Tris and/or each of the buffers comprises varying concentrations of the same chemicals. In another embodiment, each buffer comprises Bis Tris, acetic acid, NaCl, and water.

In one embodiment of the invention, the first chromatography column is a Protein A column and the second chromatography column is a multi-modal resin chromatography column. In another embodiment of the invention, the first chromatography column is a multi-modal resin chromatography column and the second chromatography column is a Protein A column. In other embodiments of the invention, the method for purifying a protein from solution does not comprise any chromatography step that comprises passing the solution over an anion-exchange chromatography (AEX) column.

In one embodiment of the invention, the protein being purified is an antibody. In another embodiment, the antibody is a monoclonal antibody.

In one embodiment of the invention, the method further comprises passing the crude protein eluent over a membrane adsorber after step (b). In other embodiments, the method further comprises a nanofiltration step after step (b) and/or an ultrafiltration and diafiltration step after the nanofiltration step.

In certain embodiments of the invention, the first elution buffer comprises 20 mM Bis Tris, and 20 mM NaCl, adjusted to pH 3.5 with acetic acid; the second elution buffer comprises 20 mM Bis Tris, and 20 mM NaCl adjusted to pH 4.5 with acetic acid; the equilibration buffer comprises 20 mM Bis Tris, and 20 mM NaCl, adjusted to pH 7.4 with acetic acid; and the wash and sanitation buffer comprises of 20 mM Bis Tris, and 1M NaCl adjusted to pH 7.4 with acetic acid. In other embodiments of the invention, the first elution buffer comprises 20 mM Bis Tris, and 20 mM NaCl adjusted to pH 4.5 with acetic acid; the second elution buffer comprises 20 mM Bis Tris, and 20 mM NaCl, adjusted to pH 3.5 with acetic acid; the equilibration buffer comprises 20 mM Bis Tris, and 20 mM NaCl, adjusted to pH 7.4 with acetic acid; and the wash and sanitation buffer comprises of 20 mM Bis Tris, and 1M NaCl adjusted to pH 7.4 with acetic acid.

The invention provides a kit comprising a multi-modal resin chromatography column and/or a Protein A column; and at least one buffer comprising or consisting of Bis Tris, acetic acid, NaCl, and water. In some embodiments, the kit is used for purifying a protein from solution using a method of the invention.

The invention also provides a kit comprising a multi-modal resin chromatography column and/or a Protein A column; and instructions for preparing at least one buffer comprising or consisting of Bis Tris, acetic acid, NaCl, and water. In some embodiments, the kit is used for purifying a protein from solution using a method of the invention.

The invention further provides the use of a buffer comprising or consisting of Bis Tris, acetic acid, NaCl, and water for purifying a protein from solution by at least one chromatography step. In some embodiments, the chromatography step is a multi-modal resin chromatography step and/or a Protein A chromatography step. Also provided is the use of a buffer comprising or consisting of Bis Tris, acetic acid, NaCl, and water for purifying a protein from solution by a method of the invention.

The invention further provides a method for preparing equilibration buffer comprising creating a 100 L solution with a final concentration of 20 mM Bis Tris and 20 mM NaCl; adjusting the pH of the solution to 7.4 with acetic acid; and collecting 50 L of the solution. The invention also provides a method for preparing wash and sanitation buffer comprising adjusting the pH of the remaining 50 L of solution from the preparation of the equilibration buffer to 4.5 with acetic acid; and collecting 25 L of the solution. The invention further provides a method for preparing an elution buffer comprising adjusting the pH of the remaining 25 L of solution from the preparation of the wash and sanitation buffer to 3.5 with acetic acid. The invention further provides a method for preparing an elution buffer comprising adding eq. 1M NaCl to 25 L of the solution remaining from the preparation of the elution buffer. The buffers prepared by the methods disclosed herein can be used for purifying a protein from solution using a method of the invention.

These and other features and advantages of the disclosed purification method will be more fully understood from the following detailed description taken together with the accompanying claims. It is noted that the scope of the claims is defined by the recitations therein and not by the specific discussion of features and advantages set forth in the description.

BRIEF DESCRIPTION OF DRAWINGS

The following detailed description of the embodiments of the disclosed purification method can be best understood when read in conjunction with the following drawings.

DETAILED DESCRIPTION OF ASPECTS AND EMBODIMENTS

Based on the availability of mixed mode resins (also called multi-modal resins) the inventors have developed a new purification process using only two chromatography steps. In other terms, the method comprises only two steps involving a passage over a chromatography column.

The invention pertains to a method for purifying a protein from solution comprising or consisting of:
  (a) a first chromatography step comprising:
    passing said solution over a first chromatography column;
    eluting a crude protein eluent from the first chromatography column using a first elution buffer; and
  (b) a second chromatography step comprising:
    passing the crude protein eluent obtained at the end of step (a) over a second chromatography column;
    recovering purified protein from the second chromatography column using a second elution buffer
wherein each of the buffers comprises Bis Tris.

More specifically, each of the two above chromatography steps may comprise or consist of:
  passing equilibration buffer over the chromatography column;
  passing the solution or the crude protein eluent over the chromatography column (as mentioned above);

passing equilibration buffer over the chromatography column;

optionally passing wash and sanitation buffer over the chromatography column;

optionally passing equilibration buffer over the chromatography column;

eluting the crude protein eluent or recovering purified protein from the chromatography column using an elution buffer (as mentioned above), wherein each of the buffers comprises Bis Tris.

As indicated above, the above method of the invention only comprises two chromatography steps. More specifically, the method may be devoid of a chromatography step that comprises passing the solution over an anion-exchange chromatography (AEX) column, and/or of a chromatography step for polishing. Even though the method according to the invention only comprises two chromatography steps, it allows obtaining purified proteins that are suitable for pharmaceutical purposes and in particular for administration to human beings.

In addition to the reduction of the number of steps in the purification process from three to two (and consequent reduction in the overall time required to complete the purification process), the disclosed method reduces the number of buffers used for purification from seven to four. In addition, the buffers comprise the same components (i.e. Bis Tris, NaCl, acetic acid and water), which greatly facilitates buffer preparation. The disclosed purification method also simplifies mAb purification, improves the overall yield, and reduces raw materials, cost of goods and process time, in addition to allowing for the purification of a variety of mAbs.

In contrast with conventional protein purification methods, as stated above, the method disclosed herein uses four buffers: an equilibrium buffer, a wash buffer, and two elution buffers. The buffers used in the disclosed method are made with the same matrix of compounds, from a mother solution, which largely facilitates buffer preparation.

As used herein, "buffers according to the invention" refer to buffers comprising Bis Tris. Bis Tris is a compound well known to the skilled in the art, the IUPAC name of which is 2-[bis(2-hydroxyethyl)amino]-2-(hydroxymethyl)propane-1,3-diol, and the CAS Number of which is 6976-37-0. Such buffers according to the invention may correspond to an equilibrium buffer, to a wash and sanitation buffer, and/or to an elution buffer.

More specifically, such buffers according to the invention may comprise or consist of varying concentrations of the same chemicals (one of them being Bis Tris). In a specific embodiment, the buffers comprise or consist of Bis Tris, acetic acid and water. In a more specific embodiment, the buffers comprise or consist of Bis Tris, acetic acid, NaCl and water. In other terms, such buffers comprise or consist of varying concentrations of Bis Tris, acetic acid, NaCl, and water.

The elution buffer may for example comprise or consist of 15 to 25 mM (e.g. 20 mM) Bis Tris, and 15 to 25 mM (e.g. 20 mM) NaCl, adjusted to a pH comprised between 3 and 4 (e.g. 3.5) with acetic acid. Such an elution buffer is notably suitable for use with an affinity chromatography column such as a Protein A column.

The elution buffer may also comprise or consist of 15 to 25 mM (e.g. 20 mM) Bis Tris, and 15 to 25 mM (e.g. 20 mM) NaCl, adjusted to a pH comprised between 4 and 5 (e.g. 4.5) with acetic acid. Such an elution buffer is notably suitable for use with a multi-modal resin chromatography column such as e.g. CAPTO ADHERE (multimodal anion exchange column, GE Healthcare).

The elution buffer may also comprise or consist of 15 to 25 mM (e.g. 20 mM) Bis Tris, and 150 to 250 mM (e.g. 200 mM) NaCl, adjusted to a pH comprised between 8 and 9 with acetic acid. Such an elution buffer is notably for use with a multi-modal resin chromatography column such as e.g. CAPTO MMC (multimodal cation exchange column, GE Healthcare).

The equilibration buffer may comprise or consist of 15 to 25 mM (e.g. 20 mM) Bis Tris, and 15 to 25 mM (e.g. 20 mM) NaCl, adjusted to a pH comprised between 7 and 8 (e.g. 7.4) with acetic acid.

The wash and sanitation buffer may comprise or consist of 15 to 25 mM (e.g. 20 mM) Bis Tris, and 0.9 to 1.1 mM (e.g. 1M) NaCl adjusted to a pH comprised between 7 and 8 (e.g. 7.4) with acetic acid.

More specifically, one equilibration buffer for use in the disclosed method contains 20 mM Bis Tris and 20 mM NaCl, adjusted to pH 7.4 with 2 mM acetic acid. One wash buffer for use in the disclosed contains 20 mM Bis Tris and 1M NaCl, adjusted to pH 7.4 with 2 mM acetic acid. A first elution buffer for use in the disclosed method contains 20 mM Bis Tris and 20 mM NaCl, adjusted to pH 3.5 with 275 mM acetic acid. A second elution buffer for use in the disclosed method contains 20 mM Bis Tris and 20 mM NaCl, adjusted to pH 4.5 with 35 mM acetic acid.

Advantages of the above buffer formulations include the capability for a mAb product to pass through the two chromatography columns used in the disclosed method with larger compatibility, while minimizing undesired interactions, limiting pH and conductivity drops, and promoting increased yield versus traditional purification methods. In addition to using a reduced number of buffers, another aspect of the disclosed method is the use of a Bis-Tris buffer.

The terms "polypeptide" or "protein" as used herein refer to molecules having the sequence of native proteins, that is, proteins produced by naturally-occurring and specifically non-recombinant cells, or genetically-engineered or recombinant cells, and comprise molecules having the amino acid sequence of the native protein, or molecules, having deletions from, additions to, and/or substitutions of one or more amino acids of the native sequence. In certain aspects, the protein to be purified is an antibody.

The term "antibody" as used herein refers to an intact antibody, or a binding fragment thereof that competes with the intact antibody for specific binding. Binding fragments include, but are not limited to, F(ab), F(ab'), F(ab')$_2$, Fv, and single-chain antibodies. The term "heavy chain" includes any immunoglobulin polypeptide having sufficient variable region sequence to confer specificity for an antigen.

The term "heavy chain" as used herein encompasses a full-length heavy chain and fragments thereof. A full-length heavy chain includes a variable region domain, VH, and three constant region domains, CH1, CH2, and CH3. The VH domain is at the amino-terminus of the polypeptide, and the CH3 domain is at the carboxyl-terminus.

The term "light chain" as used herein encompasses a full-length light chain and fragments thereof. A full-length light chain includes a variable region domain, VL, and a constant region domain, CL. Like the heavy chain, the variable region domain of the light chain is at the amino-terminus of the polypeptide. The term "light chain" as used herein includes any immunoglobulin polypeptide having sufficient variable region sequence to confer specificity for an antigen.

Naturally occurring antibody structural units typically comprise a tetramer. Each such tetramer typically is composed of two identical pairs of polypeptide chains, each pair having one full-length light chain (typically having a molecular weight of about 25 kDa) and one full-length heavy chain (typically having a molecular weight of about 50-70 kDa). The amino-terminal portion of each light and heavy chain typically includes a variable region of about 100 to 110 or more amino acids that typically is responsible for antigen recognition. The carboxy-terminal portion of each chain typically defines a constant region responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids.

The variable regions of each light/heavy chain pair typically form the antigen-binding site. The variable regions typically exhibit the same general structure of relatively conserved framework regions (FR) joined by three hypervariable regions, also called complementarity determining regions or CDRs. The CDRs from the two chains of each pair typically are aligned by the framework regions, which may enable binding to a specific epitope. From N-terminal to C-terminal, both light and heavy chain variable regions typically comprise the domains FR1, CDR1, FR2, CDR2, FR3, CDR3, and FR4. The assignment of amino acids to each domain is typically in accordance with the definitions of Kabat et al., 1991, Sequences of Proteins of Immunological Interest, 5th ed., U.S. Department of Health and Human Services, NIH Publication No. 91-3242. A bispecific or bifunctional antibody typically is an artificial hybrid antibody having two different heavy chain/light chain pairs and two different binding sites.

A F(ab) fragment is comprised of one light chain and the CH1 and variable regions of one heavy chain. The heavy chain of a F(ab) molecule cannot form a disulfide bond with another heavy chain molecule. A F(ab') fragment contains one light chain and one heavy chain that contains more of the constant region, between the CH1 and CH2 domains, such that an interchain disulfide bond can be formed between two heavy chains to form an F(ab')$_2$ molecule. The Fv region comprises the variable regions from both the heavy and light chains, but lacks the constant regions. Single-chain antibodies are Fv molecules in which the heavy and light chain variable regions have been connected by a flexible linker to form a single polypeptide chain, which forms an antigen-binding region. A bivalent antibody other than a "multispecific" or "multifunctional" antibody, in certain embodiments, is understood to comprise binding sites having identical antigenic specificity.

Monoclonal antibodies (mAbs) that can be purified by the disclosed method can be produced by a variety of techniques, including conventional monoclonal antibody methodology, e.g., the standard somatic cell hybridization technique well known in the art. Although somatic cell hybridization procedures are preferred, in principle, other techniques for producing monoclonal antibodies can be employed, e.g., viral or oncogenic transformation of B-lymphocytes. The monoclonal antibody may for instance correspond to a murine, a chimeric, a humanized or a fully human antibody.

In a specific embodiment, the antibody purified by the method of the invention is a monoclonal antibody selected from the group consisting of a an antibody that specifically binds to the protofibrillar form of the human β-amyloid protein (e.g. a humanized antibody), an antibody that specifically binds to the bacterial surface polysaccharide poly-N-acetyl glucosamine (PNAG) (e.g. a fully human antibody), and an antibody that specifically binds to the CD38 transmembrane glycoprotein (e.g. a humanized antibody).

The phrase "recovering the protein" as used herein refers to collecting a protein after using the disclosed purification method. The disclosed purification method can be achieved using a variety of standard protein chromatography techniques, such as, but not limited to, affinity chromatography, ion exchange chromatography, hydrophobic interaction chromatography, gel filtration chromatography, and multimodal resin chromatography.

In certain embodiments of the disclosed method, the first or second chromatography column is a Protein A column. The Protein A column functions via affinity between the resin ligand and the protein, resulting in high efficiency removal of impurities. Another advantage of using a Protein A column in the disclosed method is that mAbs have universal affinity toward Protein A. In one embodiment of the disclosed method, the Protein A column is MABSELECT SURE resin (Protein A resin, GE Healthcare).

In additional embodiments of the disclosed method, the first or second chromatography column is a multi-modal (mixed-mode) resin chromatography column. The multi-modal resin interacts with the protein of interest through several mechanisms with mAb:ionic, hydrophobic and hydrogen bond interactions. More specifically, in a multi-modal resin chromatography column, the mAb:ionic interaction is a mAb:cationic interaction, as opposed to mAb:anionic interactions that occur in a classical anion exchange chromatography (AEX) column.

In one specific embodiment of the disclosed method, the multi-modal resin is CAPTO ADHERE resin (multimodal anion exchange column, GE Healthcare). CAPTO ADHERE is a multimodal anion exchanger with a highly cross-linked agarose base matrix. The characteristics of CAPTO ADHERE are summarized below (see GE Healthcare Life Sciences, data file 28-9078-88 AC).

| | |
|---|---|
| Matrix | highly cross-linked agarose |
| Functional group | multimodal strong anion exchanger |
| Total ionic capacity | 0.09 to 0.12 mmol Cl−/mL medium |
| Particle size | 75 μm ($d_{50v}$) |
| Flow velocity | At least 600 cm/h in a 1-m diameter column with 20-cm bed height at 20° C. using process buffers with the same viscosity as water at <3 bar (0.3 MPa) |
| pH-stability | |
| short-term | 2 to 14 |
| long-term | 3 to 12 |
| Working temperature | +4° C. to +30° C. |

In another specific embodiment of the disclosed method, the multi-modal resin is CAPTO MMC resin (multimodal cation exchange column, GE Healthcare). CAPTO MMC is a multimodal cation exchanger with a highly cross-linked agarose base matrix. The characteristics of CAPTO MMC are summarized below (see GE Healthcare Life Sciences, data file 11-0035-45 AA).

| | |
|---|---|
| Matrix | highly cross-linked agarose |
| Functional group | multimodal weak cation exchanger |
| Total ionic capacity | 0.07-0.09 mmol H+/ml medium |
| Particle size | 75 μm (d50v) |
| Flow velocity | at least 600 cm/h in a 1 m diameter column with 20 cm bed height at 20° C. using process buffers with the same viscosity as water at <3 bar (0.3 MPa). |
| Dynamic binding | >45 mg BSA/ml medium at 30 mS/cm |
| pH-stability | |
| short-term | 2 to 14 |
| long-term | 2 to 12 |
| Working temperature | +4° C. to +30° C. |

The method according to the invention may or may not comprise adjusting the pH of the crude protein eluent using a Bis Tris solution at the end of the first chromatographic step.

In a first embodiment, the pH of the crude protein eluent using a Bis Tris solution at the end of the first chromatographic step, for instance to a pH comprised between 6 and 7 (e.g. 6.5). Such a Bis Tris solution may be a 1M Bis Tris solution. In such a method, the multi-modal resin chromatography column may for instance correspond to a CAPTO ADHERE (multimodal anion exchange column, GE Healthcare) column. A specific example of this method is disclosed in Examples 3 to 6.

In a second embodiment, the crude protein eluent obtained at the end of the first chromatographic step is directly passed over the second chromatography column. More specifically, no treatment (such as pH adjustment, buffer exchange or dilution) is then carried out between the two steps. In such a method, the multi-modal resin chromatography column may for instance correspond to a CAPTO MMC (multimodal cation exchange column, GE Healthcare) column. Additionally, the crude protein eluent may be passed over a membrane adsorber after the second chromatographic step, as further described below. A specific example of this method is disclosed in Example 7. In such a method, inter-step treatments requiring manual intervention and opening of the purification system (e.g., dilution in an inactivation vessel, post inactivity filtration and pH adjustment in a Protein A pool vessel) are totally absent.

The method disclosed herein can be used to recover purified proteins. As used herein, "purified" refers to a purity that allows for the effective use of the protein in vitro, ex vivo, or in vivo. For a protein to be useful in in vitro, ex vivo, or in vivo applications, it should be substantially free of contaminants, other proteins, and/or chemicals that could interfere with the use of that protein in such applications, or that at least would be undesirable for inclusion with the protein of interest. Such applications include that preparation of therapeutic compositions, the administration of the protein in a therapeutic composition, and other methods disclosed herein. Preferably, a "purified" protein, as referenced herein, is a protein that can be produced by any method (i.e., by direct purification from a natural source, recombinantly, or synthetically), and that has been purified from other protein components such that the protein comprises at least about 80% weight/weight of the total protein in a given composition, and more preferably, at least about 85%, and more preferably at least about 90%, and more preferably at least about 91%, and more preferably at least about 92%, and more preferably at least about 93%, and more preferably at least about 94%, and more preferably at least about 95%, and more preferably at least about 96%, and more preferably at least about 97%, and more preferably at least about 98%, and more preferably at least about 99% weight/weight of the total protein in a given composition.

As used herein, "crude protein" refers to a protein that can be produced by any method (i.e., by direct purification from a natural source, recombinantly, or synthetically), and that has been purified from other protein components such that the protein comprises less than about 80% weight/weight of the total protein in a given composition.

In one embodiment, the disclosed method additionally comprises a third step, referred to as "step (c)", in which the crude protein eluent is passed over a membrane adsorber after step (b). In particular, step (c) may be carried out when the crude protein eluent obtained at the end of the first chromatographic step is directly passed over the second chromatography column. A membrane adsorber is a form of chromatography matrix or filter that uses membranes with large pores rather than microporous particles. These pores cover the whole filter area and facilitate a very rapid flow rate of the sample, as well as optimal binding of the target molecules within the internal structure of the membrane. The membranes can be incorporated into spin columns, which allow for easy and selective separation of target proteins from complex solutions. The benefits of using a membrane adsorber are that they are as efficient as conventional chromatography processes for binding contaminants; they allow for high processing flow rates, they require no packing, validation or cleaning, and are disposable but can be reused. Salt-tolerant membranes allow for even more types of purification. In certain embodiments, the membrane adsorber is a salt tolerant interaction chromatography membrane adsorber (e.g. a SARTORIUS STIC (Sartorius) membrane adsorber) or a Q membrane adsorber.

When purifying recombinant proteins for pharmaceutical purposes, the chromatographic steps are typically followed by filtration steps. Therefore, the method of the invention may further comprise a nanofiltration step after step (b) or (c). An ultrafiltration and diafiltration step may further be carried out after the nanofiltration step. As used herein, "ultrafiltration" or "UF" refers to a filtration technique using a semi-permeable membrane to physically and selectively remove particles and/or ions from a solution based on particle size and size of the pores in the UF membrane. As used herein, "nanofiltration" refers to filtration of a solution through a nanofilter that is used to remove, e.g., viral particles. As used herein, "diafiltration" refers a technique that uses ultrafiltration membranes to completely remove, replace, or lower the concentration of salts or solvents from solutions.

Finally, the purified protein may be formulated into a composition suitable for storage, and/or into a pharmaceutical composition suitable for administration to animals and/or humans.

One of the numerous advantages of the disclosed method is that it allows obtaining good yields of highly pure protein. The purified protein that recovered with the method of the invention can for instance exhibit a purity of at least 95%, 96%, 97%, 98% or 99%. In addition, the method of the invention can allow recovering the purified with a yield of at least 85%, 90%, 95%, 96%, 97%, 98% or 99%.

Another aspect of the invention pertains to a method for preparing buffers suitable for use in the method of the invention. Indeed, all these buffers can very easily and rapidly be prepared starting from a single mother solution.

Figure 1:
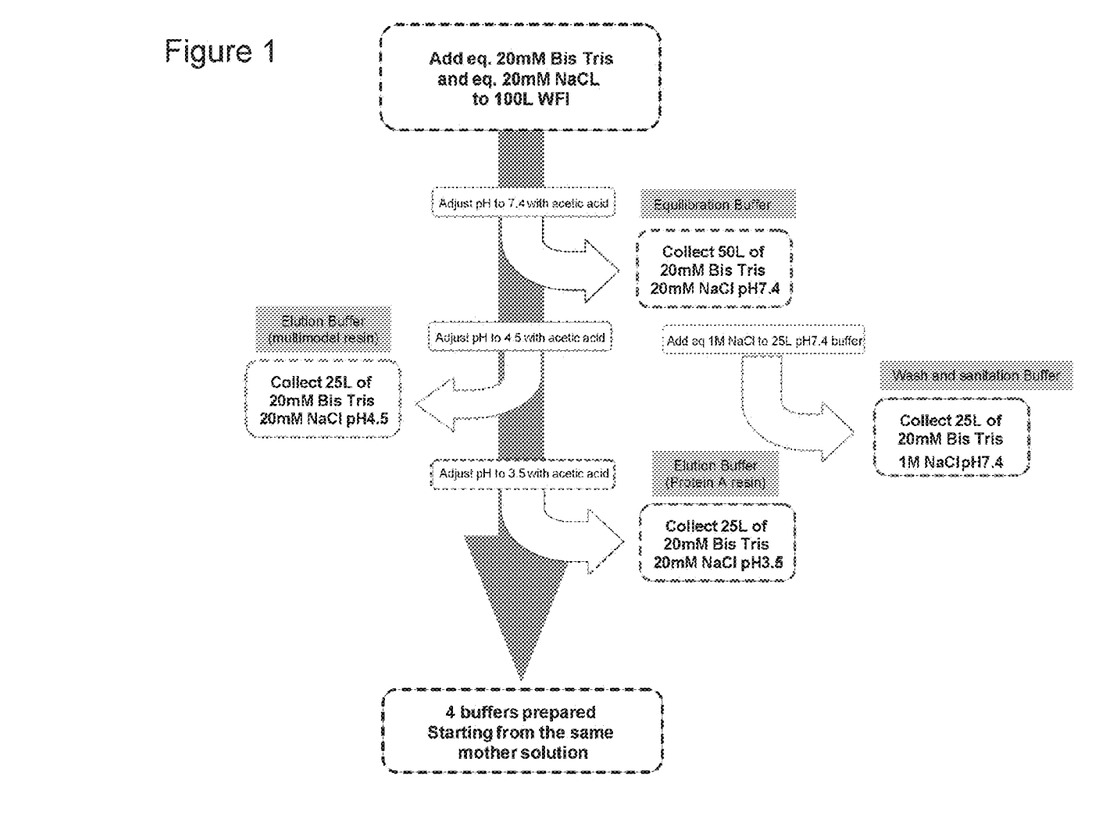
FIG. 1 shows a schematic of the protocol used to formulate the buffers of the purification method disclosed in Examples 3 to 6.

Such a method for preparing buffers may comprise or consists of the steps of:
i) creating a solution (e.g. a solution of 100 L) with a final concentration of 15 to 25 mM (e.g. 20 mM) Bis Tris and of 15 to 25 mM (e.g. 20 mM) NaCl;
ii) adjusting the pH of the solution to a value comprised between 7 and 8 (e.g. 7.4) with acetic acid;
iii) collecting half of the solution, thereby obtaining an equilibration buffer;
iv) adjusting the pH of the remaining half of solution from step (iii) to a value comprised between 4 and 5 (e.g. 4.5) with acetic acid;
v) collecting half of the solution obtained at step (iv), thereby obtaining an elution buffer.
vi) adjusting the pH of the remaining half of solution from step (v) to a value comprised between 3 and 4 (e.g. 3.5) with acetic acid, thereby obtaining a further elution buffer.
vii) collecting half of the equilibration buffer obtained at step (iii) and adding NaCl to obtain a final NaCl concentration comprised between 0.9 to 1.1 mM (e.g. 1M), thereby obtaining a wash and sanitation buffer.

Such a method is schematically depicted on FIG. 1.

Figure 6:
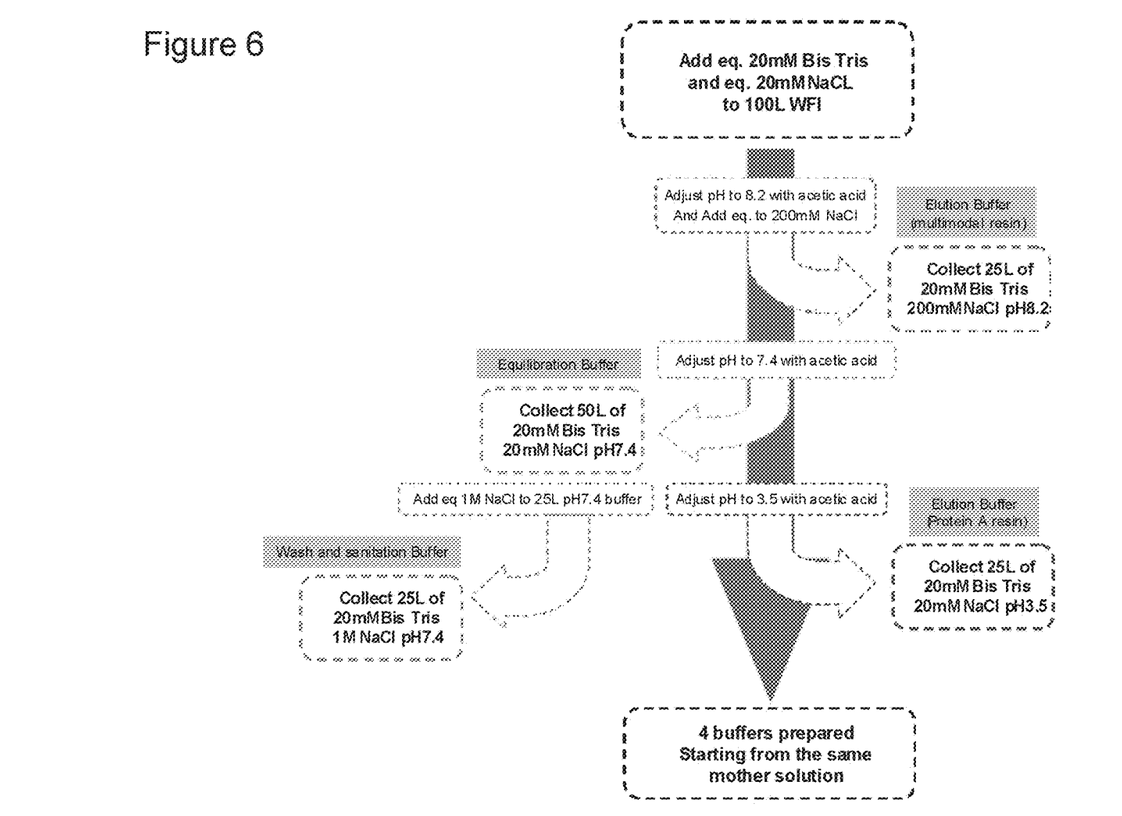
FIG. 6 shows a schematic of the protocol used to formulate the buffers of the purification method disclosed in Example 7.

Alternatively, the method for preparing buffers may comprise or consist of:
i) creating a solution (e.g. a solution of 100 L) with a final concentration of 15 to 25 mM (e.g. 20 mM) Bis Tris and of 15 to 25 mM (e.g. 20 mM) NaCl;
ii) adjusting the pH of the solution to a value comprised between 8 and 9 (e.g. 8.2) with acetic acid;
iii) collecting one fourth (e.g. 25 L) of the solution, thereby obtaining an elution buffer;
iv) adjusting the pH of the remaining solution from step (iii) to a value comprised between 7 and 8 (e.g. 7.4) with acetic acid;
v) collecting two third of the solution obtained at step (iv), thereby obtaining an equilibration buffer.
vi) adjusting the pH of the remaining solution from step (v) to a value comprised between 3 and 4 (e.g. 3.5) with acetic acid, thereby obtaining a further elution buffer.
vii) collecting half of the equilibration buffer obtained at step (v) and adding NaCl to obtain a final NaCl concentration comprised between 0.9 to 1.1 mM (e.g. 1M), thereby obtaining a wash and sanitation buffer.

Such a method is schematically depicted on FIG. 6.

One of the above methods for preparing buffers may also correspond to the very first step of the method of the invention, before performing the two chromatographic steps.

The invention further pertains to a kit comprising or consisting of:
(a) a multi-modal resin chromatography column and/or an affinity chromatography column such as a Protein A column; and
(b) at least one buffer according to the invention (e.g. comprising or consisting of Bis Tris, acetic acid, NaCl, and water), and/or instructions for preparing at least one buffer according to the invention (e.g. comprising or consisting of Bis Tris, acetic acid, NaCl, and water).

The invention further contemplates the use of a buffer according to the invention (e.g. comprising or consisting of Bis Tris, acetic acid, NaCl, and water) for purifying a protein from solution by at least one chromatography step. More specifically, the at least one chromatography step may be a multi-modal resin chromatography step and/or an affinity chromatography step such as a Protein A column.

EXAMPLES

The Examples that follow are illustrative of specific embodiments of the disclosed method, and various uses thereof. They are set forth for explanatory purposes only, and should not be construed as limiting the scope of the invention in any way.

Example 1: Optimization of Purification Buffers 1.1. A Bis Tris Buffer can be Used as an Elution Buffer with a Protein A Column When carrying out a chromatography step with a Protein A column, the elution buffer typically consists of a citrate or a glycin buffer. Such a chromatography step with a Protein A column was carried out, using the following classical conditions
Column: MABSELECT SURE (Protein A resin, GE Healthcare) of 80 mL.
Equilibration buffer: PBS buffer at pH 7.2
Elution buffer: 100 mM sodium citrate at pH 3.0
Loading: 1 L of solution comprising 1.48 g/L of anti-CD38 mAb.

175 mL of crude protein eluent comprising 7.92 g/L of mAb was obtained after the chromatography step (1.386 g of mAb).

The inventors investigated whether the citrate buffer could be replaced with a Bis Tris buffer. The following conditions were used:
Column: MABSELECT SURE (Protein A resin, GE Healthcare) of 80 mL.
Equilibration buffer: PBS buffer at pH 7.2
Elution buffer: 100 mM Bis Tris at pH 3.5 (pH adjusted with acetic acid)
Loading: 1 L of solution comprising 1.48 g/L of anti-CD38 mAb.

The inventors obtained 200 mL of crude protein eluent comprising 6.8 g/L of mAb (1.369 g of mAb).

This shows that when performing a chromatography step with a Protein A column, the use of a Bis Tris buffer as an elution buffer allows obtaining as good results as the classical sodium citrate buffer.

1.2. Bis Tris Buffers can Advantageously be Used as Buffers with a Multi-Modal Multi-Modal Resin Chromatography Column The crude protein eluent obtained after passage through a Protein A chromatography column was then passed through a CAPTO ADHERE (multimodal anion exchange column, GE Healthcare) multi-modal resin chromatography column. To this end, the inventors first tested the following conditions:
Column: CAPTO ADHERE (multimodal anion exchange column, GE Healthcare) of 1 mL.
Equilibration buffer: 100 mM sodium citrate at pH 8.6 (80%) and 100 mM citric acid at pH 2.2 (20%), the final pH being close to 5.3.
Elution buffer: Varying concentrations of the two above buffers in order to identify where optimal elution takes place.
Wash buffer: Identical to the equilibration buffer.
Loading: 20 mL of a crude protein eluent comprising 35 mg of anti-CD38 mAb, having a pH of 5.3.

The antibody was found to be eluted during the wash step, apparently because the pH dropped. Indeed, the pH dropped momentarily from 5.3 to 4.0, before increasing to a pH of 5.3 again. The fact that the pH fell to 4.0 was sufficient for the antibody to be eluted during the wash step.

The inventors then investigated whether the use of a Bis Tris buffer could possibly avoid unwanted elution during the wash step. They tested the following conditions:

Column: CAPTO ADHERE (multimodal anion exchange column, GE Healthcare) of 1 mL.
Equilibration buffer: 20 mM Bis Tris at pH 7.0 (pH adjusted with acetic acid)
Elution buffer: 20 mM Bis Tris at pH 6.0 (pH adjusted with acetic acid)
Wash/Regeneration buffer: 20 mM Bis Tris at pH 4.0 (pH adjusted with acetic acid)
Sanitation buffer: NaOH 0.5 N
Loading: 18 mL of a crude protein eluent comprising about 30 mg of anti-CD38 mAb. This eluent came from the $2^{nd}$ chromatography described at paragraph 1.1 above. The pH of the eluent was adjusted to a pH of 7.2 with a 1 M Bis Tris solution before loading onto the CAPTO ADHERE (multimodal anion exchange column, GE Healthcare) column.

The inventors found that these conditions allowed obtaining a correct elution of the antibody. Indeed, the antibody was eluted with the Bis Tris elution buffer having a pH of 6.0. Two smaller and negligible peaks were seen during regeneration at pH 4.0 and during sanitation with NaOH.

It was further tested whether it could be beneficial to adjust the pH of the Bis Tris buffers with HCl instead of acetic acid. The following conditions were used:

Column: CAPTO ADHERE (multimodal anion exchange column, GE Healthcare) of 1 mL.
Equilibration buffer: 20 mM Bis Tris at pH 7.0 (pH adjusted with HCl 1 N).
Elution buffer: gradient with a Bis Tris buffer (20 mM, pH of 4, pH adjusted with HCl 1 N).
Loading: 10 mL of a crude protein eluent comprising about 15 mg of anti-CD38 mAb. This eluent came from the $2^{nd}$ chromatography described at paragraph 1.1 above. The pH of the eluent was adjusted to a pH of 7.2 with a 1 M Bis Tris solution before loading onto the CAPTO ADHERE (multimodal anion exchange column, GE Healthcare) column.

Using these conditions, the antibody was not eluted during the wash step. This assay therefore confirms that the use of a Bis Tris buffer allows preventing unwanted elution of the antibody during the wash step. However, the pH did not drop as quickly during the elution step when the pH was adjusted with HCl rather than with acetic acid. The elution of the antibody was thus less efficient when adjusting the pH with HCl rather than with acetic acid.

In conclusion, the inventors surprisingly found that during the multi-modal resin chromatography step, the use of equilibration and elution buffers comprising Bis Tris allows avoiding unwanted elution of the antibody during the wash and sanitation step. They further found that it was advantageous to adjust the pH of the Bis Tris buffer with acetic acid. Since the Bis Tris buffer was also found to be suitable for performing the Protein A chromatography step, the inventors have found a purification process wherein the buffers can all be made with the same matrix of compounds, which greatly facilitates buffer preparation.

Further experiments were carried out to determine the optimal pH for the equilibrium buffer, the wash buffer, and the two elution buffers, which all comprise Bis Tris as well as acetic acid for pH adjustment purposes. The inventors further unexpectedly found that NaCl could advantageously be added to the buffers. These additional experiments led to the purification buffers and protocols described in Examples 2 to 7.

Example 2: Formulation of Purification Buffers

The two-step purification method described herein utilizes four buffers: an equilibration buffer, a wash and sanitation buffer, and two elution buffers, all prepared from the same mother solution. A schematic of the protocol is shown in FIG. 1 and is as follows: eq. 20 mM Bis Tris and eq. 20 mM NaCl were brought up to 100 L water for injection (WFI) as the mother solution, and the pH of the solution was then adjusted to 7.4 using acetic acid. 50 L of the resulting solution was then collected and stored as the equilibration buffer. 25 L of the equilibration buffer was then removed and eq. 1M NaCl was added, thereby decreasing the pH to 3.5. This resulting 25 L solution was the wash and sanitation buffer. The pH of the remaining 50 L of the mother solution was then adjusted to 4.5 with acetic acid. 25 L of this solution was then collected as one of the elution buffers. The remaining 25 L of the mother solution was then pH adjusted to 3.5 using acetic acid, resulting in the other elution buffer.

Example 3: Two-Step Monoclonal Antibody Purification Process

Figure 2:
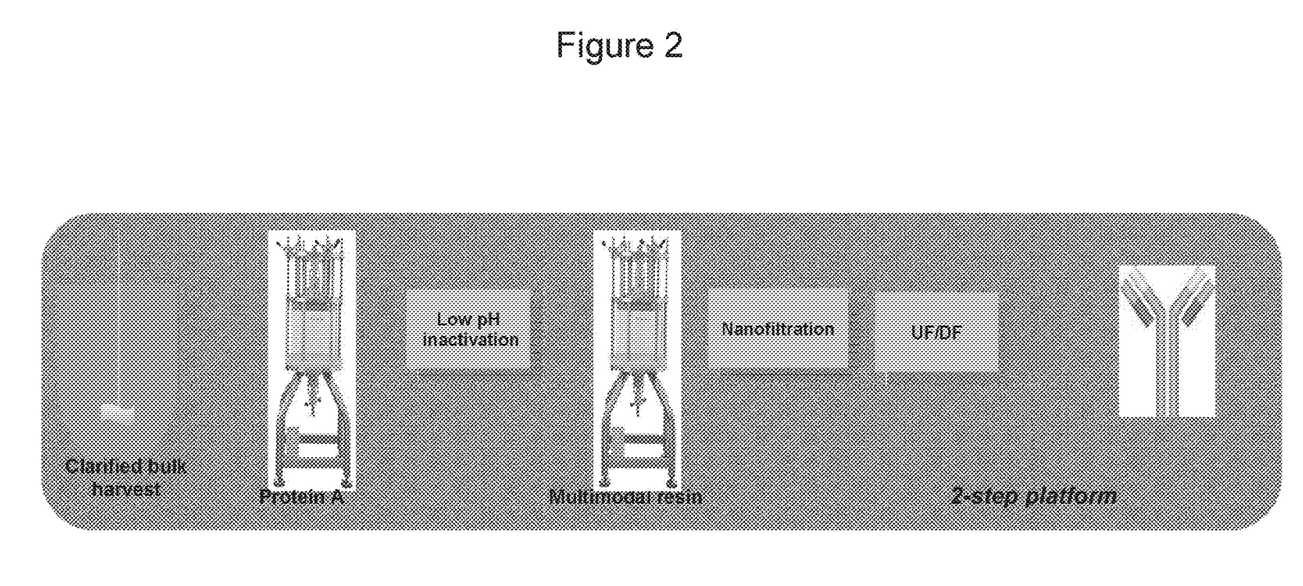
FIG. 2 shows a schematic of the two-step purification process.

The two-step monoclonal antibody (mAb) purification process is initiated with a first chromatography step using MABSELECT SURE (Protein A resin, GE Healthcare) resin. 2 column volumes (CV) of equilibration are passed over the column. The mAb solution is then loaded on the column. Two CV of wash buffer is next passed over the column, followed by two CV of equilibration buffer. The crude mAb solution is then eluted using one CV of the first elution buffer. Between the two chromatography steps is a low pH treatment. This can be a low pH adjustment using 1M acetic acid to reach pH 3.5.+−0.0.1 or a pH adjustment using 1M Bis Tris to reach pH 5.+−0.0.1. The second chromatography is conducted using a CAPTO ADHERE (multimodal anion exchange column, GE Healthcare) chromatography column. 2 CV of equilibration are passed over the column. The crude mAb solution is then loaded on the column, followed by the passing of 4 CV of equilibration buffer. The partially purified mAb solution is then eluted using one CV of the second elution buffer. Following chromatography, the mAb can be filtered with both nanofiltration and ultrafiltration/diafiltration. The nanofiltration begins with a pre-filtration step using XOHC and VPD prefilters (Millipore) and concludes with nanofiltration using a VIRESOLVE PRO filter (Millipore). Ultrafiltration is then conducted with a target concentration of 50 g/L, followed by diafiltration using 7 volumes of histidine buffer (see FIG. 2 for a schematic of the process).

Example 4: Small-Batch Purification of Humanized 13C3 mAb

The protocol described in Example 2 was utilized for small-batch purification of 53 g humanized 13C3 mAb. The 13C3 mAb binds to the protofibrillar form of the human β-amyloid protein as is described in International Publication No. WO 2009/065054.

The mAb bulk harvest was clarified through a depth filtration system and filtered using a 0.22 μm filter before storing in a 50 L disposable bag for 96 h at 2-8° C. prior to purification. 43 L of the bulk harvest was loaded on a 3.1 L MABSELECT SURE (Protein A resin, GE Healthcare) column at 240 cm/h flow-rate. The first chromatography step was performed as described above, and 6 L mAb solution was collected. Eluates were then diluted with 4 L MILLI-Q water (water purification system, Millipore) to create a solution that was ~5 g/L in concentration. The pH was then re-adjusted to 6.5 with 1 L of 1M Bis Tris. 11.03 L total volume was then filtered through a COHC grade Depth filter and a 0.22 µm MILLIPAK filter (Millipore). 11.58 L was then collected and stored at 2-8° C. For the second chromatography step, the MABSELECT SURE (Protein A resin, GE Healthcare) eluates were loaded on a 4 L CAPTO ADHERE (multimodal anion exchange column, GE Healthcare) column at 240 cm/h flow-rate. After the load step, chromatography was conducted as described above and collected in a 10 L bag with a final volume of 5.58 L. The final product was filtrated through a 0.22 µm MILLIPAK filter (Millipore) and stored at 2-8° C.

As compared to classic mAb purification, the two-step method disclosed herein returns similar results with >90% overall yield and >98% purity, in this instance, specifically 99.4% purity and a final concentration of 9.49 g/L.

Example 5: Mass Purification of Monoclonal Antibodies

The two-step purification method can also be applied to large-scale purification of monoclonal antibodies. For the first chromatography step, the bulk harvest (216 L) of humanized 13C3 mAb was split into 4 aliquots and loaded on the 3.1 L MABSELECT SURE (Protein A resin, GE Healthcare) column at 240 cm/h flow-rate in 4 runs of 54 L each. Chromatography was conducted as described above, and mAb eluates were collected in a 100 L bag. Additionally, after each load step, the column was equilibrated with equilibration buffer. The pH of the 19.7 L solution was measured to be 3.9. The eluates were then diluted to a 5 g/L concentration with 60 L of MILLI-Q water (water purification system, Millipore). The pH was then adjusted to 3.5 with 4.0 L of 1M acetic acid, lasting ~1 hour in duration. Following the pH hold, eluates were pH adjusted to pH 6.5 for the CAPTO ADHERE (multimodal anion exchange column, GE Healthcare) step with 7 L of 1M Bis Tris solution. The final volume for this step was 91 L and the product was stored at 4° C. For the second chromatography step, the MABSELECT SURE (Protein A resin, GE Healthcare) eluates were split and loaded on a 3.5 L CAPTO ADHERE (multimodal anion exchange column, GE Healthcare) column at 240 cm/h flow-rate in 4 runs. After each load step, the column was equilibrated with equilibration buffer. All elutions were pooled in the same 50 L bag through a 0.22 µm filter, and after each step, sanitization was performed using wash buffer. The final volume was 22.1 L and was stored at 2-8° C. A depth filtration step was then performed with a XOHC filter (Millipore). Due to compatibility issues between the XOHC filter and the VPF pre-filter used for the step that followed, the VPF pre-filter was added to the XOHC filter to perform filtration in the same holder. To minimize loss of yield, a Modus 1.3 nanofilter was installed in-line after the two depth filters. The solution was filtrated through 0.22 m² of XOHC grade (2×0.11 m²), 0.22 m² of VPF filter (2×0.11 m2), and the Modus 1.3 (0.21 m²). After the filtration flush, the total volume recovered was 25.9 L. No pressure problem appeared, with pressure starting at 1.8 and finishing around 1.3 bars at 460 ml/min. The final step was ultrafiltration and diafiltration of the solution. The two processes were carried out in a Millipore COGENT M (tangential flow filtration system, Millipore) with a holder that increased the capacity to 1.71 m². The batch was loaded on the COGENT M with a constant volume of 9.3 L to concentrate the solution to 50 g/L. The first concentration was reached after 50 min at 12 L/M/H pump cross flow. The diafiltration was then done with 7 volumes of 10 mM Histidine pH 6.5 in 165 min at 14 L/M/H pump cross flow. The product was then slowly concentrated over 30 min at 8 L/M/H pump cross flow. The flow was adjusted to stay under ΔP<0.6 Bars, starting at 1670 ml/min and finishing at 520 ml/min. The final volume of the collected solution was 2.6 L, containing 457 g of mAb, with a final concentration at 175.7 g/L (UV). Finally, the product was filtered using a 0.22 µm SARTAPORE 2-150 filter (Sartorius) and stored at 4° C.

Example 6: Purification of Different Monoclonal Antibodies

In addition to the humanized 13C3 antibody, the two-step purification method described above was used to purify additional antibodies, namely a fully human antibody that specifically binds to the bacterial surface polysaccharide poly-N-acetyl glucosamine (PNAG), and a humanized monoclonal antibody that specifically binds to the CD38 transmembrane glycoprotein.

The table below shows the overall yield and the purity obtained upon purification of these three antibodies.

| Antibody | Overall yield (%)[1] | Purity (%) |
|---|---|---|
| Humanized 13C3 mAb | >90 | >98 |
| Anti-PNAG mAb | >95 | >97 |
| Anti-CD38 mAb | >85 | >98 |

[1]The overall yield corresponds to the yield before the nanofiltration, ultrafiltration and diafiltration steps.

The purified humanized 13C3 mAb and the purified anti-PNAG mAb were then administered to human in the frame of clinical trials.

In conclusion, it has been confirmed with three different antibodies that the two-step purification method allows obtaining good yields of purified antibodies with an excellent degree of purity, the purified antibodies having a quality suitable for administration to human.

Example 7: "One Batch One Day" Purification Process

Figure 3:
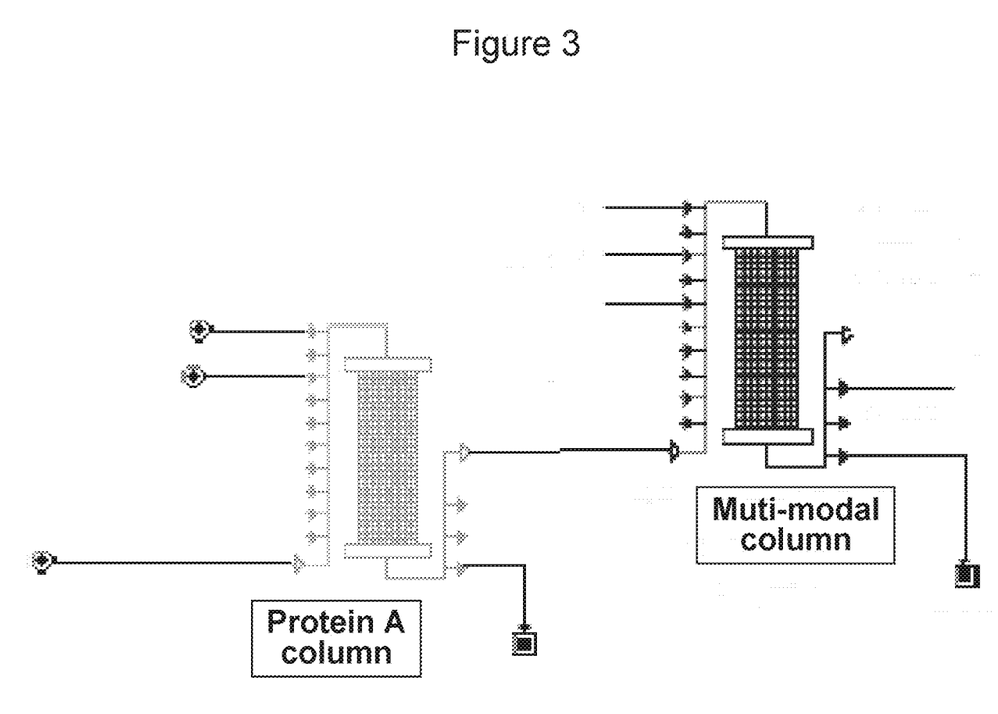
FIG. 3 shows a schematic of use of the two-step purification method for large-scale purification columns.
Figure 4:
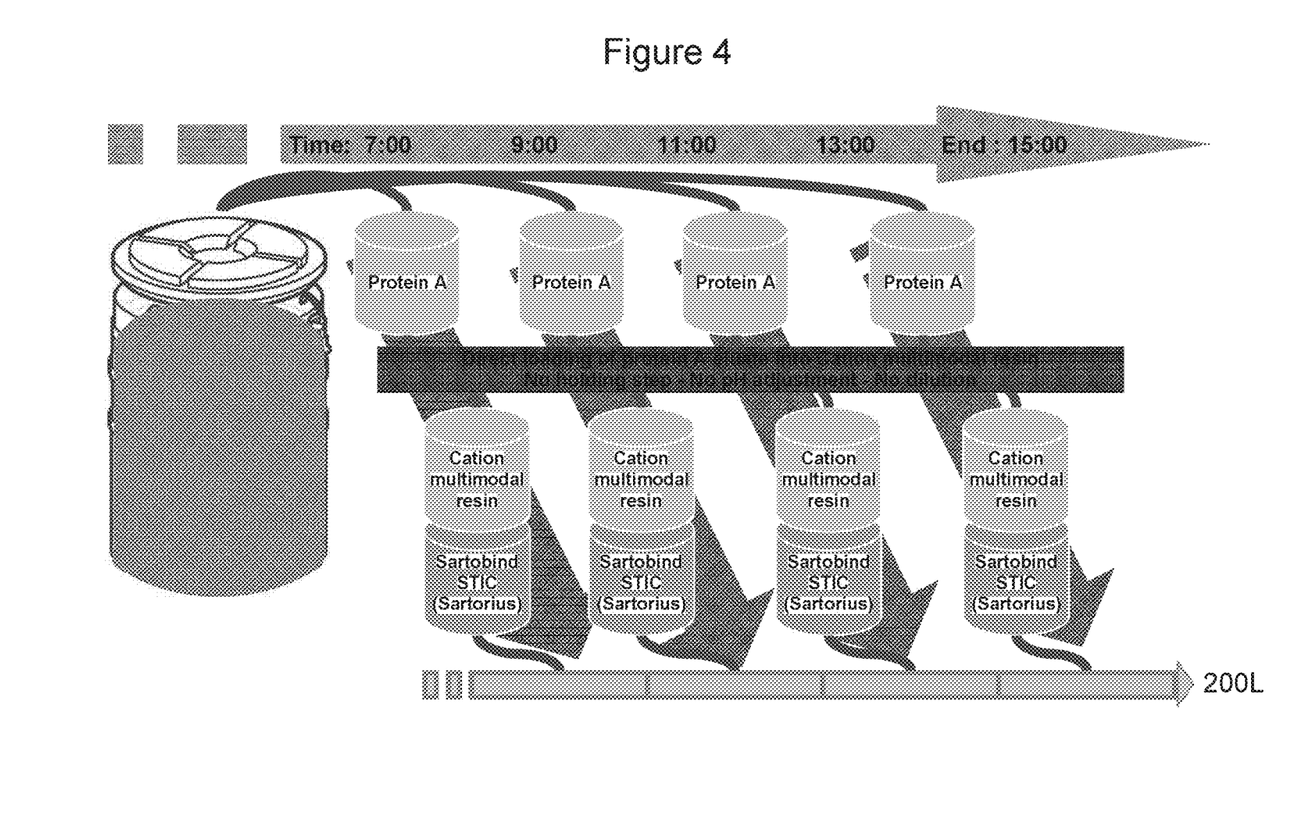
FIG. 4 shows a schematic of a "one batch one day" large-scale purification.
Figure 5:
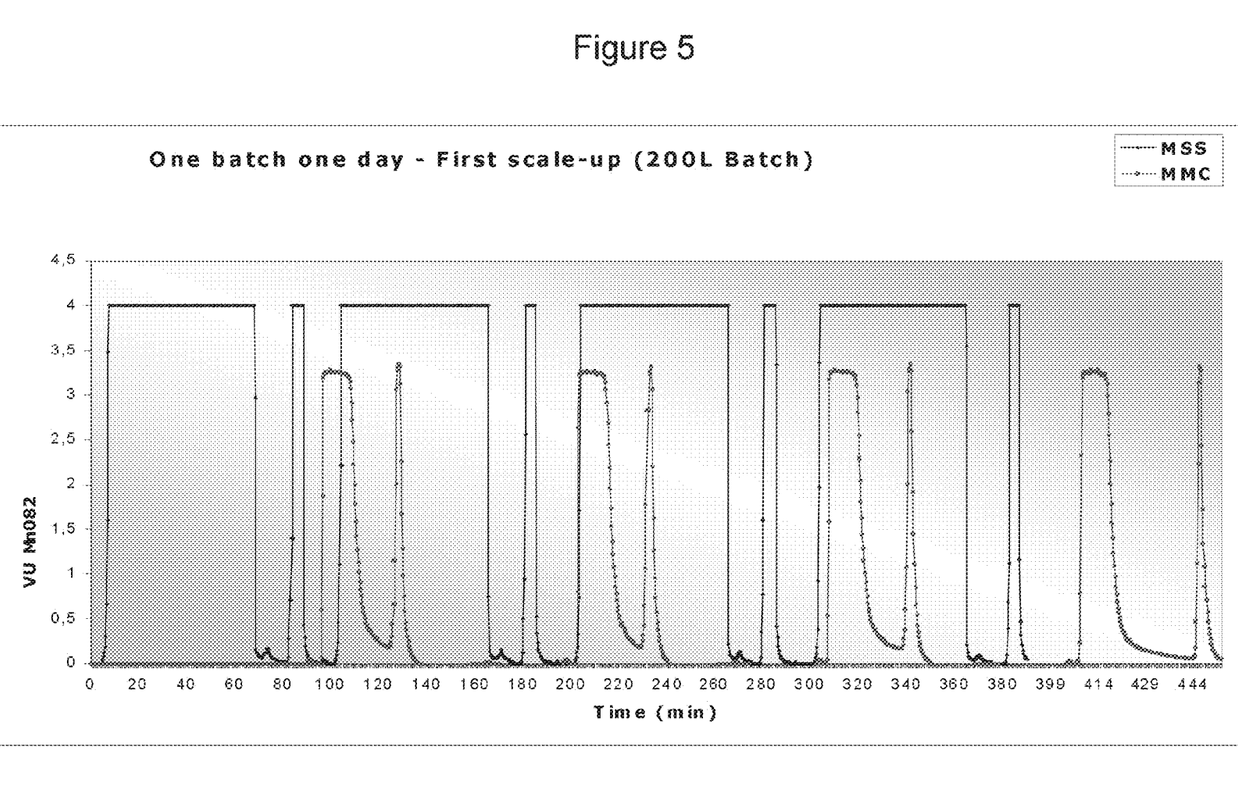
FIG. 5 shows the results of a "one batch one day" large-scale purification.

Large-scale purification can also employ the use of a Protein A column attached to a multimodal column, by passing the crude protein eluent obtained at the end of the first chromatographic step directly over the second chromatography column (see FIG. 3). Some of the benefits of using the process for large-scale purification are that further dilutions, pH adjustments, or storage is not necessary. Additionally, this method allows for rapid loading of crude antibody preps. The large-scale antibody purification method was used for purification of a 340 g batch of mAb over a 7 hour, 30 minute period (see FIG. 4). The purification method resulted in a 98% yield (332/340 g) and 96.9% purity (see FIG. 5). Additionally, contaminant removal using the method was to a similar level as seen with conventional purification methods.

The above-described large-scale purification methods can be used to meet the goals of larger and more efficient antibody preps for use in, for example, pre-clinical and clinical trials.

More specifically, this process which is called "One batch one day" was applied to a large scale purification of humanized 13C3 mAb. The aim was to purify an entire 200 L batch in one only day, through 2 chromatography steps without storage, open phase, dilution/adjustment step.

The buffers were prepared as shown in FIG. 6.

For the first chromatography step, the bulk harvest (179 L) was split into 4 aliquots and loaded on a 3.1 L MAB-SELECT SURE (Protein A resin, GE Healthcare) column in 4 runs. All the run were equilibrated with buffer B (20 mM NaCl, 20 mM Bis Tris pH7.4), washed with buffer D (1M NaCl, 20 mM Bis Tris pH7.4), and eluted with buffer C (20 mM NaCl, 20 mM Bis Tris pH3.5). Each elution was loaded directly into a 3.1 L CAPTO MMC (multimodal cation exchange column, GE Healthcare) column. Before each loading run, the column was equilibrated with buffer C (20 mM NaCl, 20 mM Bis Tris pH3.5), then after the load, the column was equilibrated with buffer B (20 mM NaCl, 20 mM Bis Tris pH7.4) and the product was eluted with buffer A (200 mM NaCl, 20 mM Bis Tris pH8.2). The entire batch was purified in one working day, from 7 am to 3 pm.

After these two chromatographic steps, all the eluted fractions were passed trough a STIC membrane before being collected in a 50 L bags.

The total volume loaded on the first column was 179 L with a mAb concentration of 1.61 g/L. The total volume purified was 35.7 L with a mAb titer of 7.26 g/L. The total yield was 90%.

Having described the invention in detail and by reference to specific embodiments thereof, it will be apparent that modifications and variations are possible without departing from the scope of the invention defined in the appended claims. More specifically, although some aspects of the invention are identified herein as particularly advantageous, it is contemplated that the invention is not necessarily limited to these particular aspects.

Each reference described and/or cited herein is incorporated by reference in its entirety.

The invention claimed is:

1. A method for purifying a monoclonal antibody or antigen binding fragment thereof from solution comprising:
    (a) a first chromatography step comprising:
        passing said solution over a first Protein A affinity chromatography column; and
        eluting a crude protein eluent from the first chromatography column using a first elution buffer; and
    (b) a second chromatography step comprising:
        passing the crude protein eluent obtained at the end of step (a) over a second chromatography column; and
        recovering purified monoclonal antibody or antigen binding fragment thereof from the second chromatography column using a second elution buffer,
        wherein each of the buffers comprises Bis Tris, acetic acid, sodium chloride (NaCl), and water.

2. The method of claim 1, wherein the method for purifying monoclonal antibody or antigen binding fragment thereof from solution only comprises two chromatographic steps.

3. The method of claim 1, wherein the second chromatography column is a multi-modal resin chromatography column.

4. The method of claim 1,
    wherein said first chromatography step comprises:
        (i) passing equilibration buffer over the first chromatography column;
        (ii) passing the solution over the first chromatography column;
        (iii) passing equilibration buffer over the first chromatography column;
        (iv) passing wash and sanitation buffer over the first chromatography column;
        (v) passing equilibration buffer over the first chromatography column;
        (vi) eluting a crude protein eluent from the first chromatography column using the first elution buffer; and
        (vii) optionally adjusting the pH of the crude protein eluent using a Bis Tris solution; and
    wherein said second chromatography step comprises:
        (i) passing equilibration buffer over the second chromatography column;
        (ii) passing the crude protein eluent from step (a) over the second chromatography column;
        (iii) passing equilibration buffer over the second chromatography column; and
        (iv) recovering purified monoclonal antibody or antigen binding fragment thereof from the second chromatography column using the second elution buffer,
        wherein each of the buffers comprises Bis Tris, acetic acid, sodium chloride (NaCl), and water.

5. The method of claim 1, wherein said monoclonal antibody is selected from the group consisting of a monoclonal antibody that specifically binds to the protofibrillar form of the human β-amyloid protein, a monoclonal antibody that specifically binds to the bacterial surface polysaccharide poly-N-acetyl glucosamine (PNAG), and a monoclonal antibody that specifically binds to the CD38 transmembrane glycoprotein.

6. The method of claim 1, wherein the first elution buffer comprises 15 to 25 mM Bis Tris and 15 to 25 mM sodium chloride (NaCl), adjusted with acetic acid to a pH of between 3 and 4.

7. The method of claim 1, wherein the purified monoclonal antibody or antigen binding fragment thereof is recovered with a yield of at least about 85% after the second chromatography step.

8. The method of claim 1, further comprising the step of formulating the recovered purified monoclonal antibody or antigen binding fragment thereof into a pharmaceutical composition.

9. The method of claim 1, wherein the purified monoclonal antibody or antigen binding fragment thereof is recovered with a yield of at least about 95% after the second chromatography step.

10. The method of claim 1, wherein the second elution buffer:
    comprises 15 to 25 mM Bis Tris and 15 to 25 mM sodium chloride (NaCl), adjusted with acetic acid to a pH of between 4 and 5, or
    comprises 15 to 25 mM Bis Tris and 150 to 250 mM NaCl, adjusted with acetic acid to a pH of between 8 and 9.

11. The method of claim 1, further comprising, after step (b), a step (c) of passing the crude protein eluent over a membrane adsorber.

12. The method of claim 11, wherein said membrane adsorber is a salt tolerant interaction chromatography membrane adsorber.

13. The method of claim 1, further comprising a nanofiltration step after step (b).

14. The method of claim 13, further comprising an ultrafiltration and diafiltration step after the nanofiltration step.

15. The method of claim 1, wherein each one of the two chromatography steps comprises:
- passing equilibration buffer over the first or second chromatography column;
- passing the solution or the crude protein eluent over the first or second chromatography column;
- passing equilibration buffer over the first or second chromatography column;
- optionally passing wash and sanitation buffer over the first or second chromatography column;
- optionally passing equilibration buffer over the first or second chromatography column; and
- eluting the crude protein eluent or recovering purified monoclonal antibody or antigen binding fragment thereof from the first or second chromatography column using an elution buffer, wherein each of the buffers comprises Bis Tris, acetic acid, sodium chloride (NaCl), and water.

16. The method of claim 15, wherein the equilibration buffer comprises 15 to 25 mM Bis Tris and 15 to 25 mM sodium chloride (NaCl, adjusted with acetic acid to a pH of between 7 and 8.

17. The method of claim 15, wherein the wash and sanitation buffer comprises 15 to 25 mM Bis Tris and 0.9 to 1.1 mM sodium chloride £NaCl, adjusted with acetic acid to a pH of between 7 and 8.

18. A method for purifying a monoclonal antibody or antigen binding fragment thereof from solution comprising:
(a) a first chromatography step comprising:
- passing said solution over a first Protein A affinity chromatography column; and
- eluting a crude protein eluent from the first chromatography column using a first elution buffer comprising 15 to 25 mM Bis Tris, 15 to 25 mM sodium chloride (NaCl), and a pH of between 4 and 5; and
(b) a second chromatography step comprising:
- passing the crude protein eluent obtained at the end of step (a) over a second chromatography column; and
- recovering purified monoclonal antibody or antigen binding fragment thereof from the second chromatography column using a second elution buffer comprising 15 to 25 mM Bis Tris, 15 to 25 mM NaCl, and a pH of between 3 and 4.

19. The method of claim 18, wherein the pH of the first elution buffer is adjusted with acetic acid to a pH of between 4 and 5 and the pH of the second elution buffer is adjusted with acetic acid to a pH of between 3 and 4.

20. A method for purifying a monoclonal antibody or antigen binding fragment thereof from solution comprising:
(a) a first chromatography step comprising:
- passing said solution over a first Protein A affinity chromatography column; and
- eluting a crude protein eluent from the first chromatography column using a first elution buffer comprising 15 to 25 mM Bis Tris, and 15 to 25 mM sodium chloride (NaCl), adjusted with acetic acid to a pH of between 4 and 5; and
(b) a second chromatography step comprising:
- passing the crude protein eluent obtained at the end of step (a) over a second chromatography column; and
- recovering purified monoclonal antibody or antigen binding fragment thereof from the second chromatography column using a second elution buffer comprising 15 to 25 mM Bis Tris, 15 to 25 mM NaCl, adjusted with acetic acid to a pH of between 3 and 4.

* * * * *

UNITED STATES PATENT AND TRADEMARK OFFICE
CERTIFICATE OF CORRECTION

PATENT NO. : 10,131,714 B2
APPLICATION NO. : 14/360103
DATED : November 20, 2018
INVENTOR(S) : Duthe et al.

It is certified that error appears in the above-identified patent and that said Letters Patent is hereby corrected as shown below:

In the Claims

Column 19, Line 21, Claim 16, delete "(NaCl" and insert --(NaCl)--.

Column 19, Line 25, Claim 17, delete "£NaCl" and insert --(NaCl)--.

Signed and Sealed this
Ninth Day of July, 2019

Andrei Iancu
*Director of the United States Patent and Trademark Office*